United States Patent [19]

Krapcho et al.

[11] 3,994,900

[45] Nov. 30, 1976

[54] 6-(OR 8)-[[(SUBSTITUTED AMINO)ALKYL]OXY(OR THIO)]-3,4-DIHYDRO-4-PHENYL-2(1H)-QUINOLINONES

[75] Inventors: John Krapcho; Joseph Schwartz, both of Somerset, N.J.

[73] Assignee: E. R. Squibb & Sons, Inc., Princeton, N.J.

[22] Filed: Jan. 23, 1976

[21] Appl. No.: 651,880

[52] U.S. Cl. .................... 260/286 R; 260/247.1 L; 260/247.2 A; 260/268 BQ; 260/286 Q; 260/288 A; 260/289 K; 424/258
[51] Int. Cl.² ...................... C07D 215/22
[58] Field of Search ........ 260/289 R, 286 R, 286 Q, 260/247.1 L, 247.2 A, 288 A, 268 BQ, 289 K

[56] References Cited
UNITED STATES PATENTS

| | | | |
|---|---|---|---|
| 3,201,401 | 8/1965 | Krapcho | 260/293.58 |
| 3,330,823 | 7/1967 | Bernstein et al. | 260/286 Q |
| 3,493,570 | 2/1970 | Plostnieks | 260/289 R |
| 3,514,459 | 5/1970 | Ritter et al. | 260/289 K |
| 3,635,985 | 1/1972 | Nishimura et al. | 260/289 K |
| 3,910,924 | 10/1975 | Tamura et al. | 260/289 K |

*Primary Examiner*—Paul M. Coughlan, Jr.
*Attorney, Agent, or Firm*—Lawrence S. Levinson; Merle J. Smith; Donald J. Barrack

[57] ABSTRACT

Quinolinones having the formula

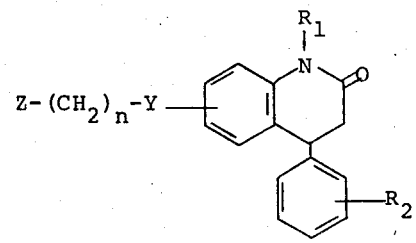

and the acid-addition and quaternary ammonium salts thereof, wherein $R_1$ is hydrogen, alkyl or arylalkyl; $R_2$ is hydrogen, halogen, trifluoromethyl, alkyl, alkoxy or nitro; Y is O, S, SO or $SO_2$; Z is alkylamino, dialkylamino, 1-pyrrolidinyl, 1-piperidinyl, 4-morpholinyl, 4-alkyl-1-piperazinyl, 4-arylalkyl-1-piperazinyl or 4-hydroxyalkyl-1-piperazinyl; and $n$ is 2, 3, 4 or 5; have useful antidepressant activity.

25 Claims, No Drawings

6-(OR 8)-[[(SUBSTITUTED AMINO)ALKYL]OXY(OR THIO)]-3,4-DIHYDRO-4-PHENYL-2(1H)-QUINOLINONES

SUMMARY OF THE INVENTION

Compounds having the formula

I

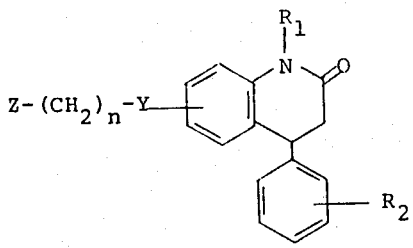

and the pharmaceutically acceptable acid-addition and quaternary ammonium salts thereof, have useful antidepressant activity. In formula I, and throughout the specification, the symbols are as defined below.

$R_1$ can be hydrogen, alkyl or arylalkyl;

$R_2$ can be hydrogen, halogen, trifluoromethyl, alkyl, alkoxy or nitro;

Y can be O, S, SO or $SO_2$;

Z can be alkylamino, dialkylamino, 1-pyrrolidinyl, 1-piperidinyl, 4-morpholinyl, 4-alkyl-1-piperazinyl, 4-arylalkyl-1-piperazinyl or 4-hydroxyalkyl-1-piperazinyl; and n is 2, 3, 4 or 5.

The basic group (i.e., $Z-(CH_2)_n-Y-$) can be in the 6- or 8-position of the quinolinone nucleus.

The terms "alkyl" and "alkoxy", as used throughout the specification, refer to groups having 1 to 6 carbon atoms.

The term "halogen", as used throughout the specification, refers to fluorine, chlorine, bromine and iodine.

The term "aryl", as used throughout the specification, refers to phenyl or phenyl monosubstituted with halogen, alkyl or alkoxy.

DETAILED DESCRIPTION OF THE INVENTION

The quinolinones of this invention can be prepared from compounds having the formula

II

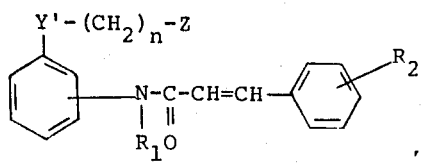

or salts thereof. In formula II, and throughout the specification, the symbol Y' can be O or S. The two side chains can be positioned ortho or para to each other. Treatment of a compound of formula II with polyphosphoric acid and heat yields a product of formula I.

Alternatively, a compound of formula I wherein $R_1$ is alkyl or arylalkyl can be prepared from the corresponding compound of formula I wherein $R_1$ is H, i.e., a compound having the formula

III

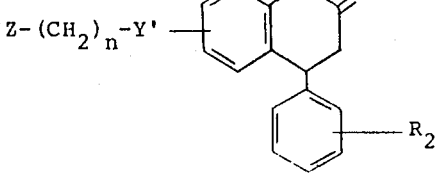

wherein the basic side chain is in the 6- or 8-position of the quinolinone nucleus. A compound of formula III can be reacted with an alkyl (or arylalkyl) halide to yield a compound of formula I wherein $R_1$ is alkyl or arylalkyl, i.e., a compound having the formula

IV

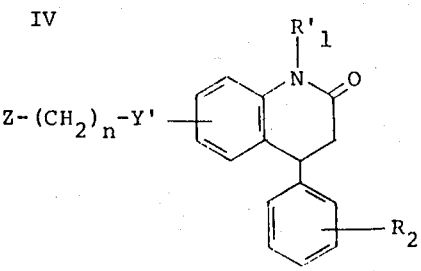

wherein the basic side chain is in the 6- or 8-position of the quinolinone nucleus, and wherein $R'_1$ is alkyl or arylalkyl.

A compound of formula I wherein Y is SO or $SO_2$ can be prepared by oxidizing the corresponding compound of formula III or IV wherein Y' is S. Oxidation of a compound of formula III or IV (wherein Y' is S) using hydrogen peroxide yields the corresponding sulfoxide derivative. Oxidation of a compound of formula III or IV (wherein Y' is S) using potassium permanganate yields the corresponding sulfonyl derivative. Alternatively, the sulfoxide and sulfonyl derivatives can be prepared by treating a compound of formula III or IV (wherein Y' is S) with m-chloroperbenzoic acid. Treatment with a single equivalent of m-chloroperbenzoic acid for 2 to 24 hours at room temperature yields the corresponding sulfoxide derivative. Treatment with two equivalents of m-chloroperbenzoic acid for 2 to 24 hours at room temperature (or for a shorter time with slight heating) yields the corresponding sulfonyl derivative.

The compounds of formula II can be prepared as described in Krapcho et al., *Jour. Med. Chem.*, 9:809 (1966) and in U.S. Pat. No. 3,201,401 issued Aug. 17, 1965 to John Krapcho. The compounds are prepared from ortho or para hydroxy or mercapto aniline, i.e., a compound having the formula

V

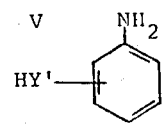

or from compounds having the formula

Va

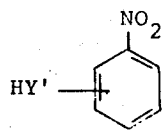

A compound of formula V or Va can be reacted with a compound having the formula

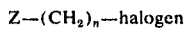

Z—(CH$_2$)$_n$—halogen  (VI)

to yield an intermediate having the formula

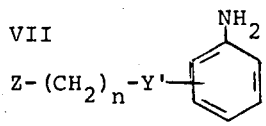

VII    Z-(CH$_2$)$_n$-Y'-⟨NH$_2$ phenyl⟩ or

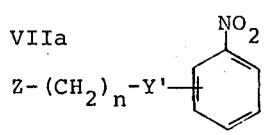

VIIa   Z-(CH$_2$)$_n$-Y'-⟨NO$_2$ phenyl⟩

The reaction can be run in a polar organic solvent, such as dimethylformamide, in the presence of a base, such as sodium hydride. If the nitrobenzene starting material of formula Va is used, the intermediate of formula VIIa should be reduced to the corresponding compound of formula VII before proceeding further. Reaction of an intermediate of formula VII with a cinnamoyl halide having the formula

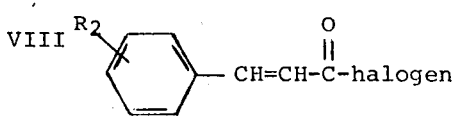

VIII   R$_2$-⟨phenyl⟩-CH=CH-C(=O)-halogen yields the starting compounds of formula II. The reaction can be run in an organic solvent, preferably a halogenated organic solvent.

The quinolinones of formula I form acid addition salts with inorganic and organic acids. Illustrative are the hydrohalides, especially the hydrochloride and hydrobromide which are preferred, sulfate, nitrate, phosphate, borate, acetate, tartrate, maleate, citrate, succinate, benzoate, ascorbate, salicylate, methanesulfonate, benzenesulfonate, toluenesulfonate and the like.

Additionally, the quinolinones of formula I form quaternary ammonium salts with alkyl halides (e.g., methyl chloride, isobutyl bromide, dodecyl chloride and cetyl iodide), benzyl halides (e.g., benzyl chloride), and dialkyl sulfates (e.g., dimethyl sulfate).

The quinolinones of formula I and the pharmaceutically acceptable acid-addition salts and quaternary ammonium salts thereof, are useful for relieving depression in mammals, in a manner similar to imipramine, when administered in a daily dose of from 0.5 mg/kg to 3 mg/kg, preferably 1 mg/kg to 2 mg/kg. The compounds of this invention reverse tetrabenazine-induced ptosis in the mouse.

The compounds of the present invention can be administered orally, for example, with an inert diluent or with an assimilable edible carrier, or they can be enclosed in hard or soft gelatin capsules, or they can be compressed into tablets, or they can be incorporated directly with the food of the diet. For oral therapeutic administration, the active compounds of this invention can be incorporated with excipients and used in the form of tablets, troches, capsules, elixirs, suspensions, syrups, wafers, chewing gum, and the like. Such compositions and preparations should contain at least 0.1% of active compound. The percentage in the compositions and preparations can, of course, be varied and can conveniently be between about 4% to about 75% or more of the weight of the unit. The amount of active compound in such therapeutically useful compositions or preparations is such that a suitable dosage will be obtained. Preferred compositions or preparations according to the present invention are prepared so that an oral dosage unit form contains between about 5 and 250 milligrams of active compound.

The tablets, troches, pills, capsules and the like can also contain the following: a binder such as gum tragacanth, acacia, corn starch or gelatin; and excipient such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it can contain in addition to materials of the above type a liquid carrier such as a fatty oil. Various other materials can be present as coatings or to otherwise modify the physical form of the dosage unit, for instance, tablets, pills, or capsules can be coated with shellac, sugar, or both. A syrup or elixir can contain the active compounds, sucrose as a sweetening agent, methyl and propyl parabens as preservatives, a dye and a flavoring such as cherry or orange flavor. Of course, any material used in preparing any dosage unit form should be pharmaceutically pure and non-toxic in the amounts employed.

The following examples are specific embodiments of this invention.

EXAMPLE 1

8-[[3-(Dimethylamino)propyl]thio]-3,4-dihydro-4-phenyl-2(1H)-quinolinone

2'-(3-Dimethylaminopropylthio)cinnamanilide, hydrochloride (30.0g) is mixed with polyphosphoric acid (700g) with stirring and heating. The temperature is allowed to reach 130°–145° C where the mixture is maintained for 15 minutes. After cooling to 60° C, the mixture is poured onto 2 liters of crushed ice and gradually treated with 1 kg. of potassium carbonate (foaming is partially controlled by addition of ethanol and ether). The basic solution is extracted with 200 ml of ether-100 ml of chloroform (3 times). The organic phases are combined, washed with 100 ml of water, dried over magnesium sulfate, filtered and the filtrate evaporated to give 24.2 g of a syrupy residue. Distillation of this material gives 17.7 g of distillate; boiling point 120°–220° C(0.1 mm of Hg). Subsequent fractionation gives 3.2 g of forerun, 2-(3-dimethylaminopropylthio)aniline, boiling point 120°–140° C(0.1 mm of Hg) and 14.0 g of pale yellow distillate; boiling point 170°–190° C(0.1 mm of Hg). This material partly solidifies and is crystallized from 5 ml of isopropanol to give 10.7 g of colorless solid, melting point 57°–80° C. After crystallization from 10 ml of acetonitrile, the material weighs 9.5 g, melting point 57°–90° C. The melting point indicates that this material is a mixture and an attempt is made to separate the mixture as a salt. A solution of 9.4 g of the base in 100 ml of chloroform is treated with 4.0 ml of 6.9 N ethanolic hydrogen chloride. The resulting yellow solution is diluted to 400 ml with ether to give a yellow amorphous product weighing 9.2 g, melting point 145°–147° C (sintering 130° C). Since this material is only partly soluble in water, a separation of this mixture is attempted by suspending 8.3 g of material in 150 ml of water. After 30 minutes, the solid is filtered, air-dried (wt. 2.3 g, melting point 104°–106° C), and the filtrate is made basic by the addition of a solution of 10 g of potassium carbonate in 20 ml of water. The liberated base is extracted with 100 ml of chloroform-200ml of ether (twice), the organic phases combined, dried over magnesium sulfate, filtered and the filtrate concentrated to give 5.0 g of the title compound, melting point 64°–66° C.

EXAMPLE 2

8-[[3-(Dimethylamino)propyl]thio]-3,4-dihydro-4-phenyl-2(1H)-quinolinone, hydrochloride (1:1)

A solution of 8-[[3-(dimethylamino)propyl]thio]-3,4-dihydro-4-phenyl-2(1H)-quinolinone (5.0g) in 50 ml of chloroform is treated with 2.1ml of 6.9N ethanolic hydrogen chloride and the resulting solution is slowly diluted to 200 ml with ether to yield 5.5g of a colorless solid, melting point 179°–181° C. After crystallization from 70 ml of acetonitrile, the product weighs 5.0g, melting point 181°–183° C.

EXAMPLE 3

8-[2-(Dimethylamino)ethoxy]-3,4-dihydro-4-phenyl-2(1H)-quinolinone, hydrochloride (1:1)

A mixture of 2'-(2-dimethylaminoethoxy)cinnamanilide, hydrochloride (15g) and polyphosphoric acid (375g) is stirred and heated at 130°–140° C for 15 minutes. After cooling to 80° C, the mixture is poured over 1 liter of ice, stirred well and basified with the gradual addition of 450g of potassium carbonate. The crude product is extracted into 500 ml of 50% ether/-chloroform, dried over magnesium sulfate and concentrated to a dark oil (13.0g).

The oil is dissolved in benzene and chromatographed over 350g of Woelm alumina IV. Elution with 600 ml of benzene removes 2.7g of impurities (oil). Elution with 1 liter of chloroform gives 5.6g of an oil. Trituration of this material with isopropyl ether yields 5.3g of a solid (melting point 74°–78° C) which cannot be purified by recrystallization.

A solution of 4.3g of the solid in 100 ml of ether is treated with an ether solution of 1 equivalent of oxalic acid to give 5.1g of solid, melting point 150°–155° C, dec. Crystallization from 30 ml of acetonitrile yields 3.5g of material, melting point 161°–163° C. Recrystallization from 20 ml of acetonitrile gives 2.8g of crystalline product, melting point 165°–167° C.

The above is dissolved in water and treated with an excess of potassium carbonate to liberate the base into ether. After drying, the solvent is evaporated to leave 2.1g of an oil which solidifies. A solution of this base in chloroform is treated with one equivalent of ethanolic hydrogen chloride. The solvent is evaporated and the residue is triturated with ether to form a gelatinous solid. After vacuum drying at 80° C, the crude product (1.8g, melting point 110°–114° C) is crystallized from 6 ml of acetonitrile to give 1.5g of crystalline product, melting point 223°–225° C.

EXAMPLE 4

6-[3-(Dimethylamino)propoxy]-3,4-dihydro-4-phenyl-2(1H)-quinolinone a. 4-[3-(Dimethylamino)propoxy]benzeneamine A stirred solution of 65.4g (0.60 mole) of p-aminophenol in 250 ml of dimethylformamide is treated portion-wise with 28.6g (0.60 mole) of 50% sodium hydride. The temperature is maintained below 35° C during the addition, warmed to 70° C then cooled to 25° C. The mixture is treated with 5g of sodium iodide and 476 ml of a 1.89 N toluene solution of 3-dimethylaminopropyl chloride, then heated at 100°–105° C for 3 hours. The cooled mixture is poured over 500 ml of ice and extracted with 300 ml of ether (2 times). The combined solvent fractions are shaken in a separatory funnel with 150 ml of 6 N hydrochloric acid. The basic product is obtained by treating the aqueous fraction with 200g of potassium carbonate (ether extraction). After drying, the solvent is evaporated and the residue fractionated to give 25.1g of an oil, boiling point 128°–135° C/0.2 mm of Hg. (Continuation of the distillation yields 21.9g of di-alkylated material, boiling point 135°–158° C/0.2 mm of Hg).

The crude product is re-distilled over a 6 inch glass particle column. The yield of base is 21.0g, boiling point 110°–112° C/0.05 mm of Hg.

b.
N-[4-[3-(Dimethylamino)propoxy]phenyl]-3-phenyl-propenamide, hydrochloride (1:1)

A solution of 16.6g of cinnamoyl chloride in 125 ml of chloroform is cooled to 15° C and treated dropwise with a solution of 19.4g of 4-[3-(dimethylamino)-propoxy]benzenamine in 75 ml of chloroform, keeping the temperature between 15° and 20° C. After stirring for 1 hour, the mixture is heated at reflux for 1 hour, cooled to 25° C and treated with 300 ml of ether to yield 31.6g of material, melting point 253°–257° C, dec.

A solution of the above in 350 ml of boiling methanol is concentrated to approximately 275 ml, then cooled for about 16 hours to give 26.2g of crystals, melting point 259°–261° C, dec.

c.
6-[3-(Dimethylamino)propoxy]-3,4-dihydro-4-phenyl-2(1H)-quinolinone

N-[4-[3-(Dimethylamino)propoxy]phenyl]-3-phenylpropenamide, hydrochloride (22g) is mixed with polyphosphoric acid (525g) with stirring and heating. The temperature is allowed to reach 130°–145° C where the mixture is maintained for 15 minutes. After cooling to 60° C, the mixture is poured onto 2 liters of crushed ice and gradually treated with 1 kg. of potassium carbonate causing the product to separate as a semi-solid. The basic mixture is extracted with ether/-chloroform and the organic phase is washed with water, dried over magnesium sulfate and concentrated to an oil which crystallizes. Trituration with hexane gives 16.3g of crystals, melting point 134°–136° C.

EXAMPLE 5

6-[3-(Dimethylamino)propoxy]-3,4-dihydro-4-phenyl-2(1H)-quinolinone, hydrochloride (1:1)

A solution of 6-[3-(dimethylamino)propoxy]-3,4-dihydro-4-phenyl-2(1H)-quinolinone (16.3g) in 30 ml of warm ethanol is stirred and treated dropwise with one equivalent of ethanolic hydrogen chloride. At 25° C, an equal volume of ether is added and the solution is seeded and cooled to give 13.3g of crystals. Crystallization from 200 ml of acetonitrile yields 12.0g of the title compound, melting point 182°–184° C.

EXAMPLE 6

6-[2-(Dimethylamino)ethoxy]-3,4-dihydro-4-phenyl-2(1H)-quinolinone a. N,N-Dimethyl-2-(4-nitrophenoxy)ethanamine

The reaction between 70g of p-nitrophenol, 27g of sodium methylate, and 0.56 mole of 3-dimethylaminoethyl chloride (using the procedures of Example 4, part a), gives 46.5g of product as a base, boiling point 128°–132° C/0.01 mm of Hg.

b. 4-[2-(Dimethylamino)ethoxy]benzeneamine

A solution of 42.5g (0.2 mole) of N, N-dimethyl-2-(4-nitrophenoxy)ethanamine in 200 ml of ethanol is divided and reduced in a Parr apparatus using 2g of 5% palladium/charcoal in 50 ml of ethanol for each of the two reactions. The combined mixtures are filtered, the solvent is evaporated and the residue is distilled to give 32.4g (90%) of oil, boiling point 145°–148° C/0.7 mm of Hg. This material solidifies into needles, melting point 48°–50° C.

c. N-[4-[2-(Dimethylamino)ethoxy]phenyl]-3-phenyl-2-propenamide, hydrochloride (1:1)

The reaction between 27.0g of 4-[2-(dimethylamino)-ethoxy]benzenamine and 24.9g of cinnamoyl chloride (using the procedure of Example 4, part b) gives 52.0g of crystals, melting point 257°–259° C, dec. Crystallization from a solution of 500 ml of methanol and 30 ml of water yields 43.1g of product, melting point 263°–265° C.

d. 6-[2-(Dimethylamino)ethoxy]-3,4-dihydro-4-phenyl-2(1H)-quinolinone

The reaction between 30g of N-[4-[2-(dimethylamino)-ethoxy]phenyl]-3-phenyl-2-propenamide, hydrochloride and 750g of polyphosphoric acid gives 18.6g of material, melting point 128°–130° C. Crystallization from 45 ml of acetone yields 13.2g of crystals, melting point 133°–135° C.

EXAMPLE 7

6-[2-(Dimethylamino)ethoxy]-3,4-dihydro-4-phenyl-2(1H)-quinolinone, hydrochloride A solution of 6-[2-(dimethylamino)ethoxy]-3,4-dihydro-4-phenyl-2(1H)-quinolinone (13.2g) in 40 ml of methanol is treated with one equivalent of ethanolic hydrogen chloride to form 13.5g of crystals, melting point 240°–244° C. Crystallization from a solution of 100 ml of methanol and 1 ml of water gives 10.6g of product, melting point 242°–244° C.

EXAMPLE 8

6-[3-(Dimethylamino)propoxy]-1-ethyl-3,4-dihydro-4-phenyl-2(1H)-quinolinone, hydrochloride (1:1)

A stirred solution of 17.3g of 6-[3-(dimethylamino)-propoxy]-3,4-dihydro-4-phenyl-2(1H)-quinolinone in 175 ml of freshly distilled dimethylformamide is treated portionwise with 2.8g of 50% sodium hydride. The mixture is heated to 70° C and kept at this point for several minutes, then cooled to 0° C using an ice water-salt bath. The cooled mixture is treated dropwise with 6.4g of ethyl bromide. After stirring for 4 hours at −5° C to 0° C, the cooling bath is removed and the mixture is kept at room temperature for 2 hours and poured into ice water. The product is extracted with 200 ml of ether (two times). The organic fractions are combined, washed with water, dried over magnesium sulfate and evaporated to give 14.7g of an oily residue. The oil is dissolved in 75 ml of ether and treated with 50 ml of an ether solution containing 3.75g of oxalic acid to give a hygroscopic solid. Trituration of this material with warm acetone yields 12.7g of colorless solid, melting point 128°–130° C, sintering 120° C. Crystallization from 50 ml of acetonitrile gives 12.3g of crystals, melting point 128°–130° C, sintering 60° C.

A solution of the oxalate salt in 100 ml of water is treated with an excess of potassium carbonate. The base is extracted with methylene chloride, dried and the solvent is evaporated to give 9.3g of oil. A solution of this material in 75 ml of acetone is treated with one equivalent of ethanolic hydrogen chloride. After concentration to approximately one-half volume, the solution is cooled to give 6.6g of a solid, melting point 143°–145° C. Crystallization from 18 ml of acetonitrile yields 5.3g of crystals, melting point 143°–145° C.

EXAMPLE 9

6-[3-(Dimethylamino)propoxy]-3,4-dihydro-1-methyl-4-phenyl-2(1H)-quinolinone, fumarate salt (1:1)

A solution of 9.5g of 6-[3-(dimethylamino)propoxy]-3,4-dihydro-4-phenyl-2(1H)-quinolinone in 75 ml of freshly distilled dimethylformamide is treated with 1.7g of 50% sodium hydride and 4.15g of methyl iodide (using the procedure of Example 8) to give 7.5g of an oily product. The oil is dissolved in 75 ml of ether and treated with an ether solution containing 2.0g of oxalic acid to give a hygroscopic solid. Trituration of this material with warm acetone, with subsequent cooling, yields 9.4g of material, melting point 105°–110° C. Crystallization from 50 ml of acetonitrile gives 8.5g of crystals, melting point 108°–110° C, sintering 100° C.

A solution of the oxalate salt in 100 ml of $H_2O$ is treated with an excess of potassium carbonate. The base is extracted into ether, dried over magnesium sulfate and the solvent is evaporated to give 7.2g of base.

A solution of 5.5g of base in 25 ml of methanol containing 1.8g of fumaric acid is concentrated to a semisolid residue and triturated with ether to form 6.0g of solid, melting point 90°–95° C, sintering 80° C. Crystallization from 12 ml of ethanol yields 3.9g of crystals, melting point 128°–130° C.

EXAMPLE 10

1-Butyl-6-[3-(dimethylamino)propoxy]-3,4-dihydro-4-phenyl-2(1H)-quinolinone, oxalate salt (1:1)

A solution of 8.5g of 6-[3-(dimethylamino)propoxy]-3,4-dihydro-4-phenyl-2(1H)-quinolinone in 75 ml of distilled dimethylformamide is treated with 1.5g of 50% sodium hydride and 3.6g of n-butyl bromide (using the procedure of Example 8) to give 9.3g of an oily base. A solution of the base in 30 ml of 50% hexane-benzene is chromatographed over 180g of Woelm Alumina IV. Elution with 500 ml of benzene gives 7.4g of oily product. A solution of the oil (7.4g) in ether is treated with 1.75g of oxalic acid dissolved in 20 ml of ether to give 7.1g of a solid, melting point 105°–110° C, sintering 100° C. Crystallization from 30 ml of acetonitrile yields 6.7g of crystals, melting point 108°–110° C, sintering 106° C.

EXAMPLE 11

6-[3-(Dimethylamino)propoxy]-3,4-dihydro-1-phenethyl-4-phenyl-2(1H)-quinolinone, hydrochloride Utilizing the procedure of Example 8 but substituting an equivalent quantity of phenethyl bromide in place of ethyl bromide, the title compound is obtained.

EXAMPLE 12

1-(4-Chlorobenzyl)-6-[3-(Dimethylamino)propoxy]-3,4-dihydro-4-phenyl-2(1H)-quinolinone, hydrochloride Utilizing the procedure of Example 8 but substituting an equivalent quantity of 4-chlorobenzyl chloride in place of ethyl bromide, the title compound is obtained.

EXAMPLE 13

4-(2-Chlorophenyl)-8-[[3-(dimethylamino)propyl]thio]-3,4-dihydro-2(1H)-quinolinone Utilizing the procedure of Example 1 but substituting 2-chloro-2'-(3-dimethylaminopropylthio)cinnamanilide, hydrochloride for 2'-(3-dimethylaminopropylthio)cinnamanilide, hydrochloride, the title compound is obtained.

EXAMPLE 14

8-[[3-(Dimethylamino)propyl]thio]-3,4-dihydro-4-(4-fluorophenyl)-2(1H)-quinolinone Utilizing the procedure described in Example 1, but substituting 2'-(3-dimethylaminopropylthio)-4-fluorocinnamanilide, hydrochloride for 2'-(3-dimethylaminopropylthio)-cinnamanilide, hydrochloride, the title compound is obtained.

EXAMPLE 15

8-[[3-(Dimethylamino)propyl]thio]-3,4-dihydro-4-(4-trifluoromethylphenyl)-2(1H)-quinolinone Utilizing the procedure described in Example 1, but substituting 2'-(3-dimethylaminopropylthio)-4-trifluoromethyleinnamanilide, namanilide, hydrochloride for 2'-(3-dimethylaminopropylthio)-cinnamanilide, hydrochloride, the title compound is obtained.

EXAMPLE 16

8-[[3-(Dimethylamino)propyl]thio]-3,4-dihydro-4-(4-methylphenyl)-2(1H)-quinolinone Utilizing the procedure described in Example 1, but substituting 2'-(3-dimethylaminopropylthio)-4-methylcinnamanilide, hydrochloride for 2'-(3-dimethylaminopropylthio)-cinnamanilide, hydrochloride, the title compound is obtained.

EXAMPLE 17

6-[2-(Dimethylamino)ethoxy]-3,4-dihydro-4-(3-methoxyphenyl)-2(1H)quinolinone

Utilizing the procedure of Example 1, but substituting 2'-(2-dimethylaminoethoxy)-3-methoxycinnamanilide, hydrochloride for 2'-(3-dimethylaminopropylthio)cinnamanilide, hydrochloride, the title compound is obtained.

EXAMPLE 18

6-[4-(Dimethylamino)butoxy]-3,4-dihydro-4-(3-nitrophenyl)-2(1H)-quinolinone

Utilizing the procedure of Example 1 but substituting 2'-(4-dimethylaminobutoxy)-3-nitrocinnamanilide, hydrochloride for 2'-(3-dimethylaminopropylthio)cinnamanilide, hydrochloride, the title compound is obtained.

EXAMPLE 19

3,4-Dihydro-8-[[2-(methylamino)ethyl]thio]-4-phenyl-2(1H)-quinolinone

Utilizing the procedure of Example 1 but substituting 2'-(2-methylaminoethylthio)cinnamanilide, hydrochloride for 2'-(3-dimethylaminopropylthio)cinnamanilide, hydrochloride, the title compound is obtained.

EXAMPLE 20

8-[[3-(Diisopropylamino)propyl]thio]-3,4-dihydro-4-phenyl-2(1H)-quinolinone

Utilizing the procedure of Example 1, but substituting 2'-(3-diisopropylaminopropylthio)cinnamanilide, hydrochloride for 2'-(3-dimethylaminopropylthio)cinnamanilide, hydrochloride, the title compound is obtained.

EXAMPLE 21

3,4-Dihydro-4-phenyl-6-[5-(1-pyrrolidinyl)pentyloxy]-2(1H)-quinolinone

Utilizing the procedure of Example 1, but substituting 4'-[5-(1-pyrrolidinyl)pentyloxy]cinnamanilide, hydrochloride for 2'-(3-dimethylaminopropylthio)cinnamanilide, hydrochloride, the title compound is obtained.

EXAMPLE 22

3,4-Dihydro-4-phenyl-8-[[2-[(1-piperidinyl)ethyl]]thio]-2(1H)quinolinone

Utilizing the procedure of Example 1, but substituting 2'-[2-(1-piperidinyl)ethylthio]cinnamanilide, hydrochloride for 2'-(3-dimethylaminopropylthio)cinnamanilide, hydrochloride, the title compound is obtained.

EXAMPLE 23

3,4-Dihydro-8-[[3-(4-morpholinyl)propyl]thio]-4-phenyl-2(1H)quinolinone

Utilizing the procedure of Example 1, but substituting 2'-[3-(4-morpholinyl)propylthio]cinnamanilide, hydrochloride for 2'-(3-dimethylaminopropylthio)cinnamanilide, hydrochloride, the title compound is obtained.

EXAMPLE 24

3,4-Dihydro-8-[[3-(4-methyl-1-piperazinyl)propyl]thio]-4-phenyl-2(1H)quinolinone Utilizing the procedure of Example 1, but substituting 2'-[3-(4-methyl-1-piperazinyl)propylthio]cinnamanilide hydrochloride for 2'-(3-dimethylaminopropylthio)cinnamanilide hydrochloride, the title compound is obtained.

EXAMPLE 25

3,4-Dihydro-8-[[3-(4-phenethyl-1-piperazinyl)propyl]thio]-4-phenyl-2(1H)quinolinone Utilizing the procedure of Example 1, but substituting 2'-[3-(4-phenethyl-1-piperazinyl)propylthio]cinnmanilide hydrochloride for 2'-(3-dimethylaminopropylthio)cinnamanilide, hydrochloride, the title compound is obtained.

EXAMPLE 26

3,4-Dihydro-8-[[3-[4-(β-hydroxyethyl)-1-piperazinyl]propyl]-thio]-4-phenyl-2(1H)quinolinone Utilizing the procedure of Example 1, but substituting 2'-[3-[4-(β-hydroxyethyl)-1-piperazinyl]propylthio]cinnamanilide, hydrochloride for 2'-(3-dimethylaminopropylthio)cinnamanilide hydrochloride, the title compound is obtained.

EXAMPLE 27

8-[[3-(Dimethylamino)propyl]thio]-3,4-dihydro-4-phenyl-2(1H)quinolinone, S oxide A solution of 5.0g of 8-[[3-(dimethylamino)propyl]thio]-3,4-dihydro-4-phenyl-2(1H)quinolinone, hydrochloride (1:1) in 100 ml of water is treated with 5 ml of 30% hydrogen peroxide at 20° C and the solution is then heated at 40° C for 1 hour, cooled and treated with 5g of potassium carbonate. The product is extracted with 200 ml of chloroform. The chloroform solution is dried over magnesium sulfate and the solvent is evaporated to give the title compound.

EXAMPLE 28

8-[[3-(Dimethylamino)propyl]sulfonyl]-3,4-dihydro-4-phenyl-2(1H)quinolinone

A solution of 5g of 8-[[3-(dimethylamino)propyl]thio]-3,4-dihydro-4-phenyl-2(1H)quinolinone, hydrochloride (1:1) in 200 ml of chloroform is maintained at 20° C during the addition of 2 equivalents of m-chloroperbenzoic acid. After standing for 12 hours at room temperature, the mixture is treated with 100 ml of 10% potassium carbonate. The organic phase is separated, dried and the solvent is evaporated at reduced pressure to give the title compound.

EXAMPLE 29

8-[[3-(Dimethylamino)propyl]thio]-3,4-dihydro-4-phenyl-2(1H)quinolinone, methochloride A solution of 5g of 8-[[3-(dimethylamino)propyl]thio]-3,4-dihydro-4-phenyl-2(1H)quinolinone in 100 ml of acetonitrile is cooled to 15° C and treated with 10g of methyl chloride. The mixture is allowed to stand for 12 hours at room temperature and the solvent is evaporated to give the title compound.

What is claimed is:

1. A compound having the formula

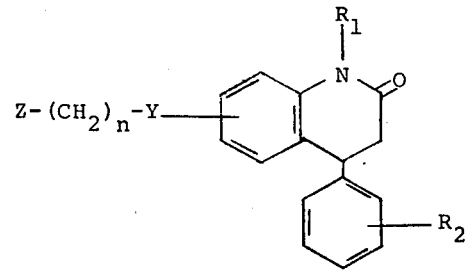

or a pharmaceutically acceptable acid-addition or quaternary ammonium salt thereof, wherein $R_1$ is hydrogen, alkyl or arylalkyl; $R_2$ is hydrogen, halogen, trifluoromethyl, alkyl, alkoxy or nitro; Y is O, S, SO or $SO_2$; Z is alkylamino, dialkylamino, 1-pyrrolidinyl, 1-piperidinyl, 4-morpholinyl, 4-alkyl-1-piperazinyl, 4-arylalkyl-1-piperazinyl or 4-hydroxyalkyl-1-piperazinyl; and $n$ is 2, 3, 4 or 5; wherein the basic group $Z—(CH_2)_n—Y—$ is in the 6- or 8-position of the quinolinone nucleus; wherein alkyl and alkoxy are groups having 1 to 6 carbon atoms and wherein aryl is phenyl or phenyl monosubstituted with halogen, alkyl or alkoxy.

2. A compound in accordance with claim 1 wherein Y is O.

3. A compound in accordance with claim 1 wherein Y is S, SO or $SO_2$.

4. A compound in accordance with claim 3 wherein Y is S.

5. A compound in accordance with claim 1 wherein $R_1$ is hydrogen.

6. A compound in accordance with claim 1 wherein $R_1$ is alkyl.

7. A compound in accordance with claim 1 wherein $R_1$ is arylalkyl.

8. A compound in accordance with claim 1 wherein $R_2$ is hydrogen.

9. A compound in accordance with claim 1 wherein $n$ is 2 or 3.

10. A compound in accordance with claim 1 wherein Z is alkylamino.

11. A compound in accordance with claim 1 wherein Z is dialkylamino.

12. A compound in accordance with claim 1 wherein Z is dimethylamino.

13. A compound in accordance with claim 1 wherein Z is 1-pyrrolidinyl, 1-piperidinyl, 4-morpholinyl, 4-alkyl-1-piperazinyl, 4-arylalkyl-1-piperazinyl or 4-hydroxyalkyl-1-piperazinyl.

14. A compound in accordance with claim 1 wherein $R_1$ and $R_2$ are hydrogen, Y is O, $n$ is 2 or 3, and Z is dialkylamino.

15. A compound in accordance with claim 1 wherein $R_1$ and $R_2$ are hydrogen, Y is S, *n* is 2 or 3, and Z is dialkylamino.

16. The compound in accordance with claim 1 having the name 8-[[3-(dimethylamino)propyl]thio]-3,4-dihydro-4-phenyl-2(1H)-quinolinone.

17. The compound in accordance with claim 1 having the name 8-[[3-(dimethylamino)propyl]thio]-3,4-dihydro-4-phenyl-2(1H)-quinolinone, hydrochloride (1:1).

18. The compound in accordance with claim 1 having the name 8-[2-(dimethylamino)ethoxy]-3,4-dihydro-4-phenyl-2(1H)-quinolinone, hydrochloride (1:1).

19. The compound in accordance with claim 1 having the name 6-[3-(dimethylamino)propoxy]-3,4-dihydro-4-phenyl-2(1H)-quinolinone.

20. The compound in accordance with claim 1 having the name 6-[3-(dimethylamino)propoxy]-3,4-dihydro-4-phenyl-2(1H)-quinolinone, hydrochloride (1:1).

21. The compound in accordance with claim 1 having the name 6-[2-(dimethylamino)ethoxy]-3,4-dihydro-4-phenyl-2(1H)-quinolinone.

22. The compound in accordance with claim 1 having the name 6-[2-(dimethylamino)ethoxy]-3,4-dihydro-4-phenyl-2(1H)-quinolinone, hydrochloride.

23. The compound in accordance with claim 1 having the name 6-[3-(dimethylamino)propoxy]-3,4-dihydro-1-methyl-4-phenyl-2(1H)-quinolinone, fumarate (1:1).

24. The compound in accordance with claim 1 having the name 6-[3-(dimethylamino)propoxy]-1-ethyl-3,4-dihydro-4-phenyl-2(1H)-quinolinone, hydrochloride (1:1).

25. The compound in accordance with claim 1 having the name 1-butyl-6-[3-(dimethylamino)propoxy]-3,4-dihydro-4-phenyl-2(1H)-quinolinone, oxalate (1:1).

* * * * *